United States Patent
Sadasivan Vijayakumari et al.

(10) Patent No.: US 9,133,077 B2
(45) Date of Patent: Sep. 15, 2015

(54) PROCESS FOR THE PREPARATION OF A LOWER OLEFIN PRODUCT

(71) Applicant: SHELL OIL COMPANY, Houston, TX (US)

(72) Inventors: Sivakumar Sadasivan Vijayakumari, Amsterdam (NL); Jeroen Van Westrenen, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 13/727,826

(22) Filed: Dec. 27, 2012

(65) Prior Publication Data

US 2013/0172652 A1 Jul. 4, 2013

(30) Foreign Application Priority Data

Dec. 27, 2011 (EP) ..................................... 11195826

(51) Int. Cl.
*C07C 1/22* (2006.01)
*C07C 1/20* (2006.01)
*C07C 4/06* (2006.01)

(52) U.S. Cl.
CPC ... *C07C 1/22* (2013.01); *C07C 1/20* (2013.01); *C07C 4/06* (2013.01); *C07C 2529/40* (2013.01); *C07C 2529/70* (2013.01)

(58) Field of Classification Search
USPC .......................................... 585/638, 639, 640
See application file for complete search history.

(56) References Cited

U.S. PATENT DOCUMENTS

| | | | |
|---|---|---|---|
| 3,270,076 A * | 8/1966 | Happel et al. ................. | 585/539 |
| 4,542,252 A * | 9/1985 | Graziani et al. .............. | 585/640 |
| 4,567,029 A | 1/1986 | Wilson et al. ................. | 502/162 |
| 4,695,560 A | 9/1987 | Gattuso et al. ................ | 502/222 |
| 6,809,227 B2 | 10/2004 | Vaughn .......................... | 585/640 |
| 2003/0109765 A1* | 6/2003 | Fung et al. .................... | 585/639 |
| 2004/0102667 A1 | 5/2004 | Vora et al. ..................... | 585/324 |
| 2005/0038304 A1 | 2/2005 | Van Egmond et al. ....... | 585/324 |
| 2006/0020155 A1 | 1/2006 | Beecii, Jr. et al. ........... | 585/639 |
| 2009/0187058 A1 | 7/2009 | Chewter et al. ............... | 585/639 |
| 2010/0206771 A1 | 8/2010 | Rothaemel et al. ............ | 208/70 |
| 2010/0261943 A1 | 10/2010 | Van Westrenen et al. .... | 585/640 |
| 2010/0268007 A1 | 10/2010 | Van Westrenen et al. .... | 585/324 |
| 2010/0268009 A1 | 10/2010 | Van Westrenen et al. .... | 585/640 |
| 2010/0298619 A1 | 11/2010 | Chewter et al. ............... | 585/639 |
| 2011/0112344 A1 | 5/2011 | Chewter et al. ............... | 585/302 |
| 2011/0160509 A1 | 6/2011 | Van Westrenen et al. .... | 585/634 |

FOREIGN PATENT DOCUMENTS

| | | | | |
|---|---|---|---|---|
| WO | WO03020667 | 3/2003 | ................ | C07C 2/08 |
| WO | WO2009065848 | 5/2009 | ................ | B01J 8/18 |
| WO | WO2009065870 | 5/2009 | ................ | B01J 8/18 |

* cited by examiner

*Primary Examiner* — In Suk Bullock
*Assistant Examiner* — Sharon Pregler

(57) ABSTRACT

A process for the preparation of an olefin product comprising ethylene, which process comprises the steps of: a) converting an oxygenate feedstock in an oxygenate-to-olefins conversion system, comprising a reaction zone in which an oxygenate feedstock is contacted with an oxygenate conversion catalyst under oxygenate conversion conditions, to obtain a conversion effluent comprising ethylene and/or propylene; b) separating at least a portion of the propylene from the conversion effluent to form a propylene stream; c) separating the remainder of the olefins from the conversion effluent; and d) recycling at least a portion of the propylene stream to step a).

9 Claims, 1 Drawing Sheet

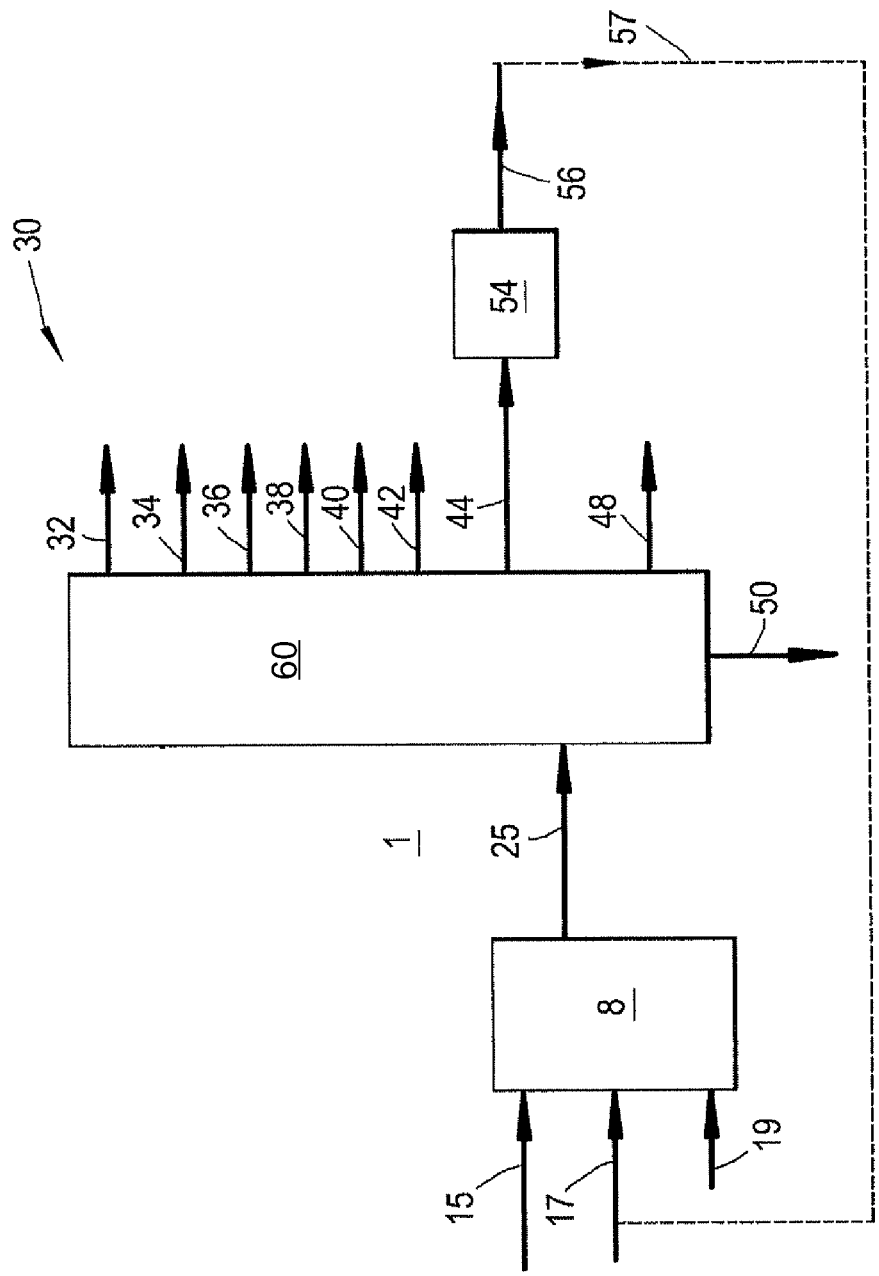

PROCESS FOR THE PREPARATION OF A LOWER OLEFIN PRODUCT

This application claims the benefit of European Patent Application No. 11195826.0, filed on Dec. 27, 2011, the disclosure of which is incorporated by reference herein in its entirety.

FIELD OF THE INVENTION

The invention relates to a process for preparing ethylene and/or other lower olefins.

BACKGROUND OF THE INVENTION

Oxygenate-to-olefin processes are well described in the art. Typically, oxygenate-to-olefin processes are used to produce predominantly ethylene and propylene. An example of such an oxygenate-to-olefin process is described in US Patent Application Publication No. 2011/112344, which is herein incorporated by reference. The publication describes a process for the preparation of an olefin product comprising ethylene and/or propylene, comprising a step of converting an oxygenate feedstock in an oxygenate-to-olefins conversion system, comprising a reaction zone in which an oxygenate feedstock is contacted with an oxygenate conversion catalyst under oxygenate conversion conditions, to obtain a conversion effluent comprising ethylene and/or propylene.

The publication further describes possible integration with a cracker. The publication also describes partially hydrogenating a $C_4$ portion of the conversion effluent and/or cracker effluent and recycling at least part of the at least partially hydrogenated $C_4$ as recycle feedstock to the cracker or oxygenate-to-olefins conversion system.

As market conditions change quite frequently, flexibility of a process system is important to its viability. This is especially important to a process that is integrated with other processes that provide feeds to the process or take outputs from the process. For example, in an oxygenate-to-olefin process, it is beneficial to be able to flexibly adjust the amount of each of the different products produced by the process. In addition, this process is typically integrated with other units so it is important to keep the feed supply constant even when product demand changes.

SUMMARY OF THE INVENTION

The invention provides a process for the preparation of an olefin product comprising ethylene, which process comprises the steps of: a) converting an oxygenate feedstock in an oxygenate-to-olefins conversion system, comprising a reaction zone in which an oxygenate feedstock is contacted with an oxygenate conversion catalyst under oxygenate conversion conditions, to obtain a conversion effluent comprising ethylene and/or propylene; b) separating at least a portion of the propylene from the conversion effluent to form a propylene stream; c) separating the remainder of the olefins from the conversion effluent; and d) recycling at least a portion of the propylene stream to step a).

BRIEF DESCRIPTION OF THE DRAWINGS

FIG. 1 depicts an embodiment of a process flow scheme in accordance with the invention.

DETAILED DESCRIPTION

Reference is made to FIG. 1, showing an embodiment of a process flow scheme for an oxygenate-to-olefins conversion process.

The process comprises an oxygenate-to-olefins (OTO) conversion system 8 and a work-up section 60. An oxygenate feedstock is fed via line 15 to the OTO conversion system 8, for example, comprising methanol and/or dimethylether. Optionally, a hydrocarbon stream and/or a diluent are fed to the OTO conversion system via lines 17 or 19, respectively.

In principle every known OTO conversion system and process can be used in conjunction with the present invention, including processes known as Methanol-to-Olefins (MtO) and Methanol to Propylene (MtP). The OTO conversion system and process can for example be as disclosed in US 2005/0038304, incorporated herein by reference; as disclosed in US 2010/206771, incorporated herein by reference; or as disclosed in US 2006/020155 incorporated herein by reference. Other particularly suitable OTO conversion processes and systems with specific advantages are disclosed in US 2009/187058, US 2010/298619, US 2010/268009, US 2010/268007, US 2010/261943, and US 2011/160509, all of which are herein incorporated by reference.

In one embodiment, molecular sieve catalysts are used to convert oxygenate compounds to light olefins. Silicoaluminophosphate (SAPO) molecular sieve catalyst may be used that are selective to the formation of ethylene and propylene. Preferred SAPO catalysts are SAPO-17, SAPO-18, SAPO-34, SAPO-35, SAPO-44, the substituted forms thereof and mixtures thereof. The oxygenate feedstock may comprise one or more aliphatic containing compounds, including alcohols, amines, carbonyl compounds, for example, aldehydes, ketones and carboxylic acids, ethers, halides, mercaptans, sulfides, and the like and mixtures thereof. Examples of suitable feedstocks include methanol, ethanol, methyl mercaptan, ethyl mercaptan, methyl sulfide, methyl amine, di-methyl ether, di-ethyl ether, methyl ethyl ether, methyl chloride, ethyl chloride, dimethyl ketone, formaldehyde, acetaldehyde and various acids such as acetic acid.

In one embodiment, the oxygenate feedstock comprises one or more alcohols having from 1 to 4 carbon atoms and most preferably methanol. The oxygenate feedstock is contacted with a molecular sieve catalyst and is converted to light olefins, preferably ethylene and propylene.

Preferably, the OTO conversion system is arranged to receive an olefin stream, and is able to at least partially convert this stream, in particular a stream comprising $C_4$ olefins, to ethylene and/or propylene. In one embodiment, the olefin can be contacted with the oxygenate conversion catalyst in the OTO reaction zone; see for example, US 2009/187058, US 2010/298619 and US 2010/268009. The oxygenate conversion catalyst preferably comprises an aluminosilicate, in particular a zeolite.

In one embodiment, an olefinic co-feed is fed to the oxygenate-to-olefins conversion system. An olefinic co-feed is a feed containing one or more olefins or a mixture of olefins. The olefinic co-feed may also comprise other hydrocarbon compounds, for example, paraffinic compounds, alkylaromatic compounds, aromatic compounds or mixtures thereof. The olefinic co-feed preferably comprises more than 25 wt % olefins, more preferably more than 50 wt %, still more preferably more than 80 wt % and most preferably in the range of from 95 to 100 wt % olefins. A preferred olefinic co-feed consists essentially of olefins. Non-olefinic compounds in the olefinic co-feed are preferably paraffinic compounds.

The olefins in the olefinic co-feed are preferably mono-olefins. Further, the olefins can be linear, branched or cyclic, but they are preferably linear or branched. The olefins may have from 2 to 12 carbon atoms, preferably 3 to 10 carbon atoms and more preferably from 3 to 8 carbon atoms.

In another embodiment, the OTO conversion system comprises an olefin cracking zone downstream from the OTO reaction zone and is arranged to crack $C_{4+}$ olefins produced in the OTO reaction zone, as described in U.S. Pat. No. 6,809,227 and US 2004/0102667, incorporated herein by reference. In one embodiment, the olefin produced in the OTO conversion system is fed to the olefin cracking zone.

In one embodiment, the yield of light olefins can be increased by converting the fraction that is heavier than propane to lighter olefins in an olefin cracking unit. The olefin cracking unit may use any molecular sieve catalyst capable of converting hydrocarbons with 4 or more carbon atoms into light olefins. Preferred molecular sieve catalysts for this olefin cracking unit are SAPO and zeolites as described hereinafter. The most preferred catalyst for this olefin cracking unit is ZSM-5.

Both the OTO process and the optional catalytic olefin cracking process may be operated in a fluidized bed or moving bed, e.g. a fast fluidized bed or a riser reactor system, and also in a fixed bed reactor or a tubular reactor. A fluidized bed or moving bed, e.g. a fast fluidized bed or a riser reactor system are preferred.

Catalysts suitable for converting the oxygenate feedstock preferably include molecular sieve-comprising catalyst compositions. Such molecular sieve-comprising catalyst compositions typically also include binder materials, matrix material and optionally fillers. Suitable matrix materials include clays, such as kaolin. Suitable binder materials include silica, alumina, silica-alumina, titania and zirconia, wherein silica is preferred due to its low acidity.

Molecular sieves preferably have a molecular framework of one, preferably two or more corner-sharing $[TO_4]$ tetrahedral units, more preferably, two or more $[SiO_4]$, $[AlO_4]$ and/or $[PO_4]$ tetrahedral units. These silicon, aluminum and/or phosphorus based molecular sieves and metal containing silicon, aluminum and/or phosphorus based molecular sieves have been described in detail in numerous publications including for example, U.S. Pat. No. 4,567,029. In a preferred embodiment, the molecular sieves have 8-, 10- or 12-ring structures and an average pore size in the range of from about 3 Å to 15 Å.

Suitable molecular sieves are silicoaluminophosphates (SAPO), such as SAPO-17, -18, 34, -35, -44, but also SAPO-5, -8, -11, -20, -31, -36, 37, -40, -41, -42, -47 and -56; aluminophosphates (AlPO) and metal substituted (silico)aluminophosphates (MeAlPO), wherein the Me in MeAlPO refers to a substituted metal atom, including metal selected from one of Group IA, IIA, IB, IIIB, IVB, VB, VIB, VIIB, VIIIB and Lanthanide's of the Periodic Table of Elements, preferably Me is selected from one of the group consisting of Co, Cr, Cu, Fe, Ga, Ge, Mg, Mn, Ni, Sn, Ti, Zn and Zr.

Alternatively, the conversion of the oxygenate feedstock may be accomplished by the use of an aluminosilicate-comprising catalyst, in particular a zeolite-comprising catalyst. Suitable catalysts include those containing a zeolite of the ZSM group, in particular of the MFI type, such as ZSM-5, the MTT type, such as ZSM-23, the TON type, such as ZSM-22, the MEL type, such as ZSM-11, the FER type. Other suitable zeolites are for example zeolites of the STF-type, such as SSZ-35, the SFF type, such as SSZ-44 and the EU-2 type, such as ZSM-48.

Aluminosilicate-comprising catalysts, and in particular zeolite-comprising catalysts, have the additional advantage that in addition to the conversion of methanol or ethanol, these catalysts also induce the conversion of olefins to ethylene and/or propylene. Furthermore, these aluminosilicate-comprising catalysts, and in particular zeolite-comprising catalysts, are particularly suitable for use as the catalyst in a catalytic olefin cracking zone. Particular preferred catalyst for this reaction, i.e. converting part of the olefins in the olefinic product, are catalysts comprising at least one zeolite selected from MFI, MEL, TON and MTT type zeolites, more preferably at least one of ZSM-5, ZSM-11, ZSM-22 and ZSM-23 zeolites.

In one preferred embodiment, the molecular sieve in the molecular sieve-comprising catalyst is a non-zeolitic molecular sieve, while part of the olefinic product, in particular at least part of the C4+ fraction containing olefins, is provided to a subsequent separate catalytic olefin cracking zone with a zeolite-comprising catalyst and the C4+ hydrocarbon fraction is at least partially converted by contact with the zeolite-comprising catalyst.

Preferred catalysts, for both the OTO reaction as well as an optional catalytic olefin cracking reaction, comprise a more-dimensional zeolite, in particular of the MFI type, more in particular ZSM-5, or of the MEL type, such as zeolite ZSM-11. Such zeolites are particularly suitable for converting olefins, including iso-olefins, to ethylene and/or propylene. The zeolite having more-dimensional channels has intersecting channels in at least two directions. So, for example, the channel structure is formed of substantially parallel channels in a first direction, and substantially parallel channels in a second direction, wherein channels in the first and second directions intersect. Intersections with a further channel type are also possible. Preferably the channels in at least one of the directions are 10-membered ring channels. A preferred MFI-type zeolite has a Silica-to-Alumina ratio SAR of at least 60, preferably at least 80.

Particular catalysts, for both the OTO reaction as well as an optional olefin cracking reaction, include catalysts comprising one or more zeolite having one-dimensional 10-membered ring channels, i.e. one-dimensional 10-membered ring channels, which are not intersected by other channels. Preferred examples are zeolites of the MTT and/or TON type. Preferably, the catalyst comprises at least 40 wt %, preferably at least 50% wt of such zeolites based on total zeolites in the catalyst.

In a particularly preferred embodiment the catalyst, for both the OTO reaction as well as an optional catalytic olefin cracking reaction, comprises in addition to one or more one-dimensional zeolites having 10-membered ring channels, such as of the MTT and/or TON type, a more-dimensional zeolite, in particular of the MFI type, more in particular ZSM-5, or of the MEL type, such as zeolite ZSM-11.

The catalyst, for both the OTO reaction as well as an optional catalytic olefin cracking reaction, may comprise phosphorus as such or in a compound, i.e. phosphorus other than any phosphorus included in the framework of the molecular sieve. It is preferred that an MEL or MFI-type zeolites comprising catalyst additionally comprises phosphorus. The phosphorus may be introduced by pre-treating the MEL or MFI-type zeolites prior to formulating the catalyst and/or by post-treating the formulated catalyst comprising the MEL or MFI-type zeolites. Preferably, the catalyst comprising MEL or MFI-type zeolites comprises phosphorus as such or in a compound in an elemental amount of from 0.05-10 wt % based on the weight of the formulated catalyst. A particularly preferred catalyst comprises MEL or MFI-type zeolites having SAR of in the range of from 60 to 150, more preferably of from 80 to 100, and phosphorus, wherein the phosphorus has preferably been introduced by post-treatment of the formulated catalyst. An even more particularly preferred catalyst comprises ZSM-5 having SAR of in the range of from 60 to 150, more preferably of from 80 to 100, and phosphorus, wherein the phosphorus has preferably been introduced by post-treatment of the formulated catalyst. The phosphorus may be introduced by impregnation of the zeolite with phosphoric acid, which is typically followed by calcination at 550° C.

It is preferred that molecular sieves in the hydrogen form are used in the oxygenate conversion catalyst in step (g), e.g., HZSM-22, HZSM-23, and HZSM-48, HZSM-5. Preferably at least 50 wt %, more preferably at least 90 wt %, still more preferably at least 95 wt % and most preferably 100 w % of the total amount of molecular sieve used is in the hydrogen form. It is well known in the art how to produce such molecular sieves in the hydrogen form.

Typically the catalyst deactivates in the course of the process, primarily due to deposition of coke on the catalyst. Conventional catalyst regeneration techniques can be employed to remove the coke. It is not necessary to remove all the coke from the catalyst as it is believed that a small amount of residual coke may enhance the catalyst performance and additionally, it is believed that complete removal of the coke may also lead to degradation of the molecular sieve. This applies to the catalyst for both the OTO reaction as well as an optional catalytic olefin cracking reaction.

The catalyst particles used in the process of the present invention can have any shape known to the skilled person to be suitable for this purpose, for it can be present in the form of spray dried catalyst particles, spheres, tablets, rings, extrudates, etc. Extruded catalysts can be applied in various shapes, such as, cylinders and trilobes. If desired, spent oxygenate conversion catalyst can be regenerated and recycled to the process of the invention. Spray-dried particles allowing use in a fluidized bed or riser reactor system are preferred. Spherical particles are normally obtained by spray drying. Preferably the average particle size is in the range of 1-200 μm, preferably 50-100 μm.

Suitable OTO processes will be further described in detail below. In the OTO conversion system 8, the oxygenate feedstock, and optionally an olefin co-feed (which can be partly or fully a recycle stream) are contacted with an oxygenate conversion catalyst under oxygenate conversion conditions, to obtain a conversion effluent comprising lower olefins in line 25. An optional diluent stream may comprise water, steam, inert gases such as nitrogen and/or paraffins, such as methane.

The reaction conditions of the oxygenate conversion include a reaction temperature of 350 to 1000° C., preferably from 350 to 750° C., more preferably 450 to 700° C., even more preferably 500 to 650° C.; and a pressure from 0.1 kPa (1 mbar) to 5 MPa (50 bar), preferably from 100 kPa (1 bar) to 1.5 MPa (15 bar).

Effluents from the OTO conversion system need to be worked up in order to separate and purify various components as desired, and in particular to separate one or more lower olefin product streams. FIG. 1 shows a work-up section 60 which receives and processes at least part of the conversion effluent.

Typically, the effluent is quenched in a quench unit with a quench medium such as water to cool the process gas before feeding it to a compressor. This allows for a smaller compressor and lower power consumption due to reduced gas volume. Any liquid hydrocarbons after the quench are phase separated from liquid water and separately recovered. The water or steam recovered from the quench unit can be partially recycled as diluent to the OTO conversion system via line 19. The water may be treated or purified, for example, to remove catalyst fines or to maintain the pH at around neutral.

The vapor components after the quench are typically sent to a compression section that can comprise multiple compression steps, subjected to a caustic wash treatment, dried and sent to a separation including a cold section, to obtain separate streams of the main components. Additional compression steps may be carried out during, or after any of the above mentioned washing and drying steps. FIG. 1 shows hydrogen stream 32, light ends stream 34 typically comprising methane and/or carbon monoxide, ethane stream 36, ethylene stream 38, propane stream 40, propylene stream 42, a $C_4$ stream 44, a $C_{5+}$ stream 48 and a water effluent 50. There can also be a separate outlet for heavy (liquid) hydrocarbons. As known to one of ordinary skill in the art, the work-up section may be designed to provide different purities of each stream, and some of the streams will be produced from the work-up section as combined streams, i.e., $C_4$, $C_5$ and $C_6$ components can be combined. Additional reaction, treatment and/or purification steps may be carried out on any of these streams. For example, methane, carbon monoxide and hydrogen may be fed to a methanator to produce methane.

It is advantageous to recycle at least part of the various streams to the OTO conversion system 8. The process of this invention comprises recycling at least a portion of the propylene to the OTO conversion system. By recycling the propylene to the OTO conversion system, the amount of $C_4$, $C_5$ and $C_6$ olefins produced will increase. This is especially beneficial if demand for propylene is reduced, i.e., when a downstream polypropylene plant is offline. This allows the plant to continue to operate at desired feed rates without producing excess propylene which is difficult to store. By maintaining feed rates, the upstream and other downstream units can continue to operate at desired feed rates without having to divert feeds or products to intermediate storage facilities. For example, an upstream unit producing methanol from methane can continue operating at normal rates even when the propylene outlet is constrained. Additionally, it is easier to store and/or transport $C_{4+}$ olefins than $C_3$ olefins so shifting of production from propylene to heavier olefins can be useful in certain situations.

Some changes may be necessary to allow the system to handle the recycle of a portion of or the entire propylene stream. Feeding propylene to the OTO reactor may require additional steam to be fed to the OTO reactor as diluent. Further, depending on the reactor capacity available, the recycle of propylene may result in a decrease in the allowable feed rate of one or more other feed components, for example, the oxygenate feedstock or olefin feed stream may need to be reduced to accommodate the propylene recycle.

Although FIG. 1 does not show the details of the workup section, the propylene is preferably recycled downstream of a propylene splitter which separates the propylene from propane and any methylacetylene and 1,2-propadiene (MAPD) present. The MAPD can be hydrogenated and the propane can be removed.

The amount of recycled propylene to the OTO conversion system is at least 3 wt %, calculated as the total feed to the OTO conversion system. The amount of recycled propylene is preferably at least 5 wt %, more preferably at least 10 wt % and most preferably at least 15 wt %. The stream comprising the recycled propylene is preferably at least 60 wt % olefinic, more preferably at least 90 wt % olefinic and most preferably at least 99 wt % olefinic.

FIG. 1 shows propylene stream 42, and a portion or this entire stream may be recycled to the OTO conversion system 8. The propylene stream could be fed with the C4 recycle via lines 57 and 17. One of ordinary skill in the art will recognize that the work-up section could be operated such that the propylene and $C_4$ stream are not separated, but fed together to the OTO conversion system.

FIG. 1 shows the $C_4$ stream 44 being fed to a hydrogenation unit 54. All or part of the $C_4$ stream may be at least partially hydrogenated with a source of hydrogen. The at least partially dehydrogenated C4 stream can be recycled to the OTO conversion system via line 57 and line 17. When recycling to the OTO, the recycle C4 stream can be a co-feed to the OTO reaction zone or it can be a feed to an optional catalytic olefin cracking zone downstream from the OTO reaction zone. Suitable catalysts and conditions are described herein, as well as in U.S. Pat. No. 6,809,227 and US 2004/0102667. Catalysts include those comprising zeolite molecular sieves such as MFI-type, e.g., ZSM-5, or MEL-type, e.g., ZSM-11, as well as Boralite-D and silicalite 2.

In one particular embodiment, the stream 44 comprises a small quantity of di-olefins, in particular butadiene. A small quantity of butadiene is for example, at least 0.01 wt % of butadiene in the stream, in particular at least 0.1 wt %, more in particular at least 0.5 wt. The stream comprising a small quantity of butadiene may be subjected to selective hydrogenation conditions in hydrogenation unit 54 to convert butadiene to butene, while preferably minimizing the hydrogenation of butene to butane. A suitable process for selective hydrogenation is described in U.S. Pat. No. 4,695,560. It is preferred for at least 90 wt % of the butadiene to be converted to butene and less than 10 wt %, preferably less than 5 wt % of the butene to be converted to butane. In another embodiment, the small quantity of butadiene may be left in the stream and recycled to the OTO conversion system.

The effluent from selective hydrogenation is a $C_4$ feedstock comprising butene, and butene is a desirable co-feed in OTO reactions, in particular in a process in which a catalyst comprising an aluminosilicate or zeolite having one-dimensional 10-membered ring channels and an olefin co-feed is employed. The butene rich effluent can be recycled via line 57b.

In the OTO process, some paraffins are formed, for example $C_4$ saturates that will build up in the system until they are removed. An optional bleed line is present to remove these paraffins from the system.

In one embodiment, the $C_5$ and/or $C_6$ olefin streams may be recycled to the OTO reactor. In another embodiment, the $C_5$ and/or $C_6$ streams may be fed to an olefin cracking unit where the olefins are cracked to lower olefins, preferably ethylene and propylene. Any propylene formed in the olefin cracking unit may also be recycled to the OTO conversion system.

The propylene may be fed to an olefin cracking unit, but it is preferably fed to the OTO conversion system to make additional ethylene and C4+ olefins. As can be seen from the examples, it is preferred to recycle propylene to the OTO conversion system. The conversion of propylene fed to an olefin cracking unit is very low so recycling propylene to the olefin cracking unit is not preferred.

EXAMPLES

Example 1

Two catalysts, comprising 40 wt % zeolite, 36 wt % kaolin and 24 wt % silica were tested to show their ability to convert propylene to an olefinic product. To test the catalyst formulations for catalytic performance, the catalysts were pressed into tablets and the tablets were broken into pieces and sieved.

In the preparation of the first catalyst sample, ZSM-23 zeolite powder with a silica to alumina molar ratio (SAR) of 46, and ZSM-5 zeolite powder with a SAR of 80 were used in the ammonium form in the weight ratio 50:50. Prior to mixing the powders, the ZSM-5 zeolite powder was treated with phosphorus, resulting in a catalyst that has only one zeolite pre-treated with phosphorus. Phosphorus was deposited on a ZSM-5 zeolite powder with a silica-to-alumina ratio of 80 by means of impregnation with an acidic solution containing phosphoric acid to obtain a ZSM-5 treated zeolite powder containing 2.0 wt % P. The ZSM-5 powder was calcined at 550° C. Then, the powder mix was added to an aqueous solution and subsequently the slurry was milled. Next, kaolin clay and a silica sol were added and the resulting mixture was spray dried wherein the weight-based average particle size was between 70-90 μm. The spray dried catalysts were exposed to ion-exchange using an ammonium nitrate solution. Then, phosphorus was deposited on the catalyst by means of impregnation using acidic solutions containing phosphoric acid ($H_3PO_4$). The concentration of the solution was adjusted to impregnate 1.0 wt % of phosphorus on the catalyst. After impregnation the catalysts were dried at 140° C. and then calcined at 550° C. for 2 hours. The final formulated catalyst thus obtained is further referred to as catalyst 1.

Another formulated catalyst was prepared as described herein above for catalyst 1, with the exception that only ZSM-5 with a SAR of 80 was used and it was not treated with phosphorus prior to spray-drying. The concentration of the phosphorus impregnation solution was adjusted to impregnate 1.5 wt % of phosphorus on the catalyst formulation. The final formulated catalyst thus obtained is further referred to as catalyst 2.

The phosphorus loading on the final catalysts is given based on the weight percentage of the elemental phosphorus in any phosphor species, based on the total weight of the formulated catalyst.

Propylene was reacted over the catalysts which were tested to determine their selectivity towards olefins, mainly ethylene and higher olefins. For the catalytic testing, a sieve fraction of 60-80 mesh was used. The reaction was performed using a quartz reactor tube of 1.8 mm internal diameter. The molecular sieve samples were heated in nitrogen to the reaction temperature and a mixture consisting of 3 vol % propylene and, in some tests, 6 vol % methanol, balanced with $N_2$ was passed over the catalyst at atmospheric pressure (1 bar).

The Gas Hourly Space Velocity (GHSV) is determined by the total gas flow over the zeolite weight per unit time (ml gas)/(g zeolite·hr). The gas hourly space velocity used in the experiments was 19,000 (ml gas)/(g zeolite·hr). The effluent from the reactor was analyzed by gas chromatography (GC) to determine the product composition. The composition was calculated on a weight basis of all hydrocarbons analyzed. The composition was defined by the division of the mass of specific product by the sum of the masses of all products. The effluent from the reactor obtained at several reactor temperatures was analyzed. The results are shown in Table 1. As can be seen from the examples converted to ethylene, $C_4$ compounds and others. This shows that a propylene recycle can effectively be used to reduce the amount of propylene produced and shift production to one of the other products of this OTO conversion. Propylene fed to an olefin cracking unit (exemplified by the examples without methanol co-feed) has a low conversion, so it is not preferred to recycle propylene to an olefin cracking unit.

TABLE 1

| Catalyst | Methanol (vol. %) | Temp (° C.) | Ethylene (wt %) | Propylene (wt %) | C4 (wt %) | C5 (wt %) | C6+ (wt %) | Light Ends (wt %) | Propylene conversion (%) |
|---|---|---|---|---|---|---|---|---|---|
| 1 | 0 | 525 | 3.27 | 88.30 | 6.29 | 0.44 | 1.33 | 0.38 | 11.70 |
| 1 | 6 | 525 | 11.75 | 57.38 | 24.50 | 2.54 | 3.42 | 0.41 | 42.62 |
| 2 | 0 | 525 | 5.31 | 82.34 | 9.61 | 0.67 | 1.70 | 0.37 | 17.66 |
| 2 | 6 | 525 | 14.25 | 56.09 | 22.61 | 2.45 | 4.11 | 0.50 | 43.91 |
| 1 | 0 | 600 | 2.76 | 91.89 | 4.11 | 0.24 | 0.74 | 0.25 | 8.11 |
| 1 | 6 | 600 | 15.69 | 57.98 | 22.05 | 1.28 | 2.35 | 0.64 | 42.02 |
| 2 | 0 | 600 | 4.93 | 86.46 | 6.30 | 0.42 | 1.56 | 0.33 | 13.54 |
| 2 | 6 | 600 | 19.02 | 56.28 | 18.78 | 1.18 | 3.69 | 1.04 | 43.72 |

Example 2

Example 2 was carried out in a similar manner to example 1 except that catalyst used in the tests was the molecular sieve itself: ZSM23 SAR46 (sample 1) and ZSM22 SAR100 (sample 2). A sieve fraction of 60-80 mesh is used for testing. The composition of the effluent is displayed in Table 2.

TABLE 2

| Sample | Methanol (vol. %) | Temp (° C.) | Ethylene (wt %) | Propylene (wt %) | C4 (wt %) | C5 (wt %) | C6+ (wt %) | Light Ends (wt %) | Propylene conversion (%) |
|---|---|---|---|---|---|---|---|---|---|
| 1 | 0 | 525 | 5.32 | 83.56 | 7.16 | 0.65 | 2.99 | 0.32 | 16.44 |
| 1 | 6 | 525 | 22.48 | 48.39 | 20.10 | 2.50 | 6.48 | 0.05 | 51.61 |
| 2 | 0 | 525 | 3.03 | 89.16 | 4.66 | 0.42 | 2.52 | 0.21 | 10.84 |
| 2 | 6 | 525 | 18.24 | 51.55 | 22.53 | 2.15 | 4.81 | 0.72 | 48.45 |
| 1 | 0 | 600 | 5.39 | 87.30 | 4.44 | 0.38 | 1.79 | 0.69 | 12.70 |
| 1 | 6 | 600 | 30.74 | 44.77 | 13.01 | 1.92 | 7.68 | 1.87 | 55.23 |
| 2 | 0 | 600 | 3.93 | 89.53 | 3.75 | 0.23 | 1.78 | 0.78 | 10.47 |
| 2 | 6 | 600 | 25.71 | 48.29 | 17.14 | 1.93 | 5.10 | 1.82 | 51.71 |

As can be seen from these results, recycled propylene fed to an OTO reactor with an oxygenate co-feed (methanol) can be

What is claimed is:

1. A process for the preparation of an olefin product comprising ethylene, which process comprises the steps of:
    a. converting an oxygenate feedstock in an oxygenate-to-olefins conversion system, comprising a reaction zone in which an oxygenate feedstock is contacted with an oxygenate conversion catalyst under oxygenate conversion conditions, to obtain a conversion effluent comprising ethylene and propylene;
    b. separating at least a portion of the propylene from the conversion effluent to form a propylene stream;
    c. separating the remainder of the olefins from the conversion effluent; and
    d. recycling at least a portion of the propylene stream to step a) wherein the amount of recycled propylene to step a) is at least 5 wt %, calculated as the total feed to the oxygenate-to-olefins conversion system.

2. A process as claimed in claim 1 wherein the recycled propylene is contacted with the oxygenate feedstock and the oxygenate conversion catalyst.

3. A process as claimed in claim 1 wherein the recycled propylene comprises propylene produced in a cracking process downstream of the oxygenate-to-olefins reaction zone.

4. A process as claimed in claim 1 wherein the conversion effluent further comprises olefins having from 4-6 carbon atoms.

5. A process as claimed in claim 1 wherein olefins other than ethylene are fed to step a) with the oxygenate feedstock.

6. A process as claimed in claim 5 wherein the olefins other than ethylene comprise olefins having from 4 to 6 carbon atoms.

7. A process as claimed in claim 1 wherein the oxygenate feedstock is selected from the group consisting of methanol, ethanol, tert-alkyl ethers and mixtures thereof.

8. A process as claimed in claim 1 wherein the amount of recycled propylene to step a) is at least 10 wt %, calculated as the total feed to the oxygenate-to-olefins conversion system.

9. A process as claimed in claim 1 wherein the amount of recycled propylene to step a) is at least 10 wt %, calculated as the total feed to the oxygenate-to-olefins conversion system.

* * * * *